United States Patent
Koizumi

(10) Patent No.: US 9,304,082 B2
(45) Date of Patent: Apr. 5, 2016

(54) INFORMATION ACQUIRING APPARATUS AND INFORMATION ACQUIRING METHOD FOR ACQUIRING INFORMATION ON SPECIMEN BY USING TERAHERTZ WAVE

(71) Applicant: CANON KABUSHIKI KAISHA, Tokyo (JP)

(72) Inventor: Takayuki Koizumi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/485,453

(22) Filed: Sep. 12, 2014

(65) Prior Publication Data

US 2015/0076354 A1    Mar. 19, 2015

(30) Foreign Application Priority Data

Sep. 17, 2013 (JP) ................................. 2013-191797
Aug. 19, 2014 (JP) ................................. 2014-166865

(51) Int. Cl.
*G01J 5/02* (2006.01)
*G01N 21/55* (2014.01)
*G01N 33/48* (2006.01)
*G01N 21/3586* (2014.01)
*G01N 21/3563* (2014.01)
*G01N 21/3581* (2014.01)

(52) U.S. Cl.
CPC ............ *G01N 21/55* (2013.01); *G01N 21/3563* (2013.01); *G01N 21/3581* (2013.01); *G01N 21/3586* (2013.01); *G01N 33/48* (2013.01); *G01N 2201/0636* (2013.01); *G01N 2201/0697* (2013.01); *G01N 2201/06113* (2013.01)

(58) Field of Classification Search
CPC .................................................. G01N 21/3586
USPC ............................................ 250/341.1–341.9
See application file for complete search history.

(56) References Cited

U.S. PATENT DOCUMENTS

| | | | | |
|---|---|---|---|---|
| 2009/0326383 | A1* | 12/2009 | Barnes et al. | 600/476 |
| 2010/0097777 | A1* | 4/2010 | Mecca | 361/814 |
| 2011/0205528 | A1* | 8/2011 | Ogawa et al. | 356/51 |
| 2011/0303847 | A1* | 12/2011 | Kurashina et al. | 250/338.4 |

FOREIGN PATENT DOCUMENTS

JP    2011-112548 A    6/2011

* cited by examiner

*Primary Examiner* — Kiho Kim
(74) *Attorney, Agent, or Firm* — Canon USA, Inc. I.P. Division

(57) ABSTRACT

An information acquiring apparatus that acquires information on a specimen by applying terahertz wave to the specimen through a plate-like member, the specimen being provided between a reflecting member having a reflecting surface and the plate-like member. The apparatus includes an applying unit that applies the terahertz wave to the specimen, a detecting unit that detects the terahertz wave reflected from the specimen, and an information acquiring unit that acquires the information on the specimen by using temporal waveforms acquired from a result of detection performed by the detecting unit, the information acquiring unit using at least a temporal waveform representing a portion of the terahertz wave that is reflected by an interface between the plate-like member and the specimen and a temporal waveform representing a portion of the terahertz wave that is reflected by an interface between the specimen and the reflecting surface of the reflecting member.

17 Claims, 9 Drawing Sheets

INFORMATION ACQUIRING APPARATUS AND INFORMATION ACQUIRING METHOD FOR ACQUIRING INFORMATION ON SPECIMEN BY USING TERAHERTZ WAVE

BACKGROUND OF THE INVENTION

1. Field of the Invention

The present invention relates to an information acquiring apparatus and an information acquiring method for acquiring information on a specimen by using terahertz wave.

2. Description of the Related Art

Terahertz wave consists of electromagnetic waves within at least part of a frequency band of 30 GHz or higher and 30 THz or lower. Terahertz time-domain spectroscopy (THz-TDS) is one of known methods of spectroscopy in which terahertz wave is used. In THz-TDS, terahertz wave is detected while the timing of an ultrashort pulse reaching a detector is changed, whereby a temporal waveform of the terahertz wave is acquired.

Such a method of THz-TDS has been applied to apparatuses and so forth in each of which information on a specimen is acquired and an image is formed by using the acquired information on the specimen. Examples of such an imaging apparatus include a reflection THz-TDS apparatus that detects radiation reflected by a surface of a specimen or an interface in the specimen.

As disclosed by Japanese Patent Laid-Open No. 2011-112548, a reflection THz-TDS apparatus employs a method in which a specimen is brought into contact with a plate-like member and terahertz wave is applied to the specimen through the plate-like member. Using the plate-like member makes the specimen flat. Furthermore, the terahertz wave that has been reflected by the front surface of the plate-like member is measurable at each of different points of application of the terahertz wave. Therefore, changes in the intensity of the terahertz wave can be standardized, which is suitable for imaging performed in a measurement of a wide area.

In Japanese Patent Laid-Open No. 2011-112548, information on the specimen is acquired by using the amount of change in the phase of the terahertz wave that has been reflected by the interface between the plate-like member and the specimen. In some cases, the amount of change in the phase may be much smaller than the phase difference caused by the terahertz wave that has traveled through the plate-like member.

In such cases, the accuracy in the acquisition of information on the specimen can be improved under the following conditions: to accurately know the thicknesses of the plate-like member at different points of application that are to be used in the compensation for the phase difference, to perform measurement by using a plate-like member having high parallelism with a tolerance of 1 μm or smaller, and so forth. However, even if such conditions are satisfied, it is not easy to completely eliminate the phase difference caused by the terahertz wave that has traveled through the plate-like member.

SUMMARY OF THE INVENTION

According to an aspect of the present invention, there is provided an information acquiring apparatus that acquires information on a specimen by applying terahertz wave to the specimen through a plate-like member, the specimen being provided between a reflecting member and the plate-like member, the reflecting member having a reflecting surface that reflects the terahertz wave. The apparatus includes an applying unit that applies the terahertz wave to the specimen, a detecting unit that detects the terahertz wave reflected from the specimen, and an information acquiring unit that acquires the information on the specimen from a result of detection performed by the detecting unit, the information acquiring unit using at least a temporal waveform representing a portion of the terahertz wave that is reflected by an interface between the plate-like member and the specimen and a temporal waveform representing a portion of the terahertz wave that is reflected by an interface between the specimen and the reflecting surface of the reflecting member.

Further aspects of the present invention will become apparent from the following description of exemplary embodiments with reference to the attached drawings.

DESCRIPTION OF THE EMBODIMENTS

First Embodiment

Figure 1:
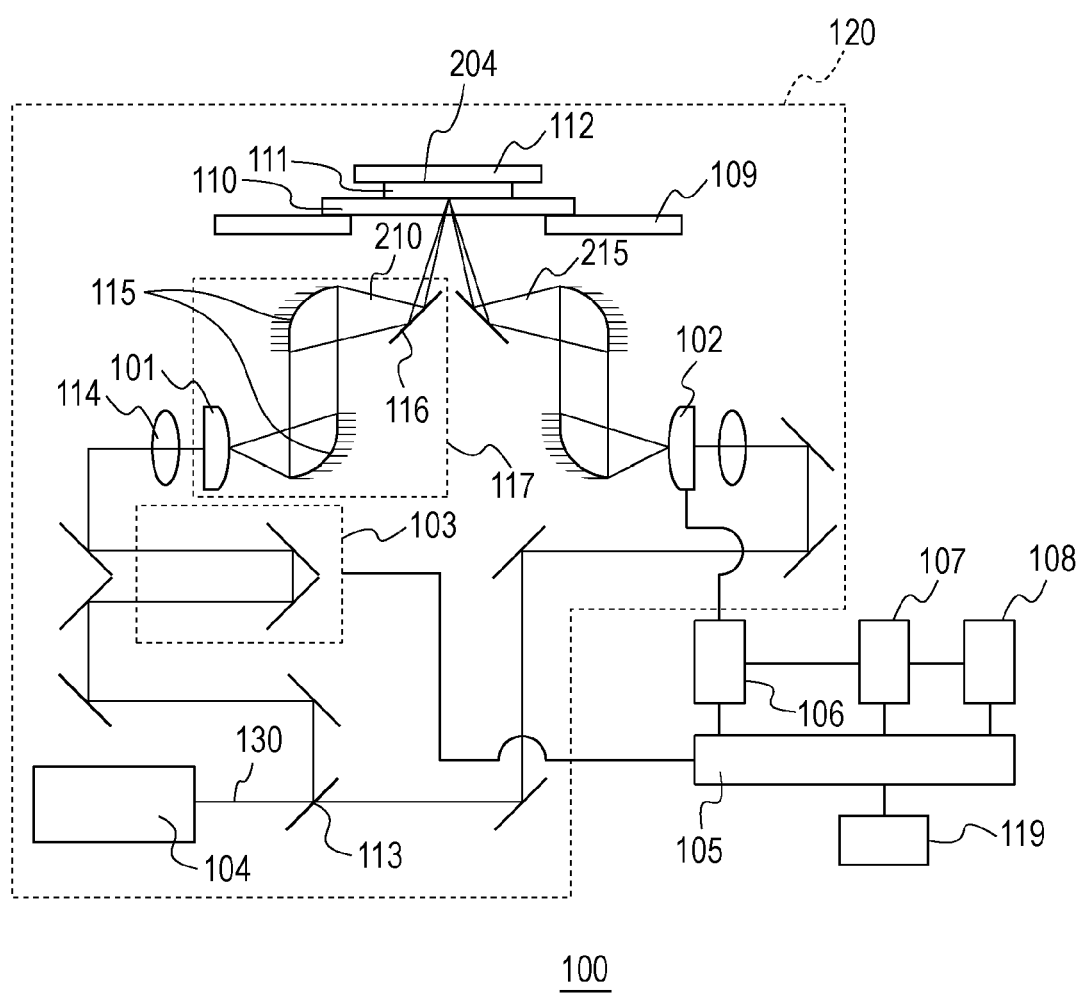
FIG. 1 is a diagram illustrating an information acquiring apparatus according to a first embodiment.

An information acquiring apparatus 100 (hereinafter referred to as "apparatus 100") according to a first embodiment will now be described with reference to FIG. 1. FIG. 1 is a diagram illustrating the apparatus 100. The apparatus 100 is an imaging apparatus that acquires information on a specimen by using terahertz wave and forms an image of the specimen on the basis of the acquired information. In the first embodiment, optical characteristics of the specimen are acquired as the information on the specimen.

The term "information on the specimen" used in this specification encompasses the shape of the specimen including the shapes of any objects in the specimen, and the shapes of any areas of the specimen that have predetermined optical characteristics; and optical characteristics of the specimen. The term "optical characteristics" used in this specification encompasses the complex amplitude reflectance, the complex refractive index, the complex dielectric constant, the reflectance, the refractive index, the absorption coefficient, the dielectric constant, the electric conductivity, and so forth of the specimen.

The apparatus 100 includes a measuring mechanism 120 that acquires a temporal waveform by applying pulsed terahertz wave (incident pulses) 210 to a specimen 111 and detecting terahertz wave 215 that has been reflected by the specimen 111. The apparatus 100 further includes a control unit 105, a waveform acquiring unit 106, an information acquiring unit 107, an image forming unit 108, and a storage unit 119.

First, the measuring mechanism 120 will be described. The measuring mechanism 120 includes a detecting unit 102, an optical delay unit 103, a light source 104, a scanning stage 109, a beam splitter 113, a lens 114, and an applying unit 117. The applying unit 117 includes a generating unit 101 that generates the pulsed terahertz wave 210, and a parabolic mirror 115 and a plane mirror 116 that guide the generated terahertz wave 210 toward the specimen 111.

The light source 104 is a pulsed-laser light source that emits an ultrashort pulsed laser beam 130 (hereinafter also referred to as laser beam 130). The laser beam 130 emitted from the light source 104 is a femtosecond laser beam. The term "ultrashort pulsed laser beam 130" used in this specification represents pulsed light having a pulse width of several hundred femtoseconds (fs) or smaller. In particular, an ultrashort pulsed laser beam having a pulse width of 1 fs or larger and 100 fs or smaller is referred to as a femtosecond laser beam.

The generating unit 101 generates the pulsed terahertz wave 210. The laser beam 130 emitted from the light source 104 is split into two beams by the beam splitter 113. One of the two beams is applied to the generating unit 101, whereby the pulsed terahertz wave (input pulse) 210 is generated. The pulsed terahertz wave 210 generated by the generating unit 101 is reflected by the parabolic mirror 115 and the plane mirror 116 and is applied to the specimen 111 through a plate-like member 110.

Methods of generating the terahertz wave 210 in the generating unit 101 include methods utilizing instantaneous carrying currents, methods utilizing interband carrier transition, and so forth. Exemplary methods utilizing instantaneous carrying currents include a method in which the terahertz wave 210 is generated by applying the laser beam 130 to a semiconductor, an organic crystal, or a nonlinear optical crystal; and a method in which an electric field is applied to a photoconductive device having an antenna pattern formed of metal electrodes provided on a semiconductor thin film, and the laser beam 130 is applied to the photoconductive device. Exemplary methods utilizing interband carrier transition include a method utilizing a semiconductor quantum well structure.

The specimen 111 is positioned between the plate-like member 110 and a reflecting member 112. More specifically, the specimen 111 is positioned such that the terahertz wave 210 reaches the reflecting member 112 after being applied to the specimen 111 through the plate-like member 110. In such a case, it is desirable that the specimen 111 be in contact with the plate-like member 110 and with the reflecting member 112, with no air gaps interposed therebetween.

If it is difficult to exclude air between the specimen 111 and the plate-like member 110 and to bring the two into full contact with each other, a matching liquid having a complex refractive index spectrum close to the complex refractive index spectrum of the specimen 111 or the plate-like member 110 may be provided between the two so as to increase the adhesion between the two. Likewise, a matching liquid having a complex refractive index spectrum close to the complex refractive index spectrum of the specimen 111 or the reflecting member 112 may be provided between the specimen 111 and the reflecting member 112 so as to increase the adhesion between the two. The layer of the matching liquid is sufficiently thinner than the wavelength of the terahertz wave 210 to be applied to the specimen 111 and is desirably ½₀ or smaller than the wavelength of the terahertz wave 210. The plate-like member 110 and the reflecting member 112 will be described in detail separately below.

The terahertz wave 215 (containing reflected pulses) that is a reflection of the terahertz wave 210 applied to the specimen 111 through the plate-like member 110 is detected by the detecting unit 102. Exemplary detecting methods using the detecting unit 102 include a method in which a current corresponding to the amplitude of the terahertz wave 215 is detected by using a photoconductive device, a method in which an electric field is detected by utilizing an electro-optical effect produced by a combination of an orthogonal polarizer and an electro-optical crystal, and a method in which a magnetic field is detected by using a combination of an orthogonal polarizer and a magneto-optical crystal. If the terahertz wave 215 incident on the detecting unit 102 is focused on the detecting unit 102, the intensity of the terahertz wave 215 per unit area is increased, whereby the sensitivity of detection can be increased.

The optical delay unit 103 adjusts the time when the terahertz wave 215 is detected by the detecting unit 102. Specifically, the optical delay unit 103 changes the relative optical path length between the laser beam 130 inputted to the detecting unit 102 and the laser beam 130 inputted to the generating unit 101. Exemplary methods of adjusting the optical path length include a method in which the optical path length is changed physically by using a folding optical system and a movable unit, a method in which the optical path length is changed by changing the refractive index or the like in a path along which the beam travels, and so forth.

In the first embodiment, the optical path length of the laser beam 130 from the light source 104 to the generating unit 101 is adjusted by using the optical delay unit 103 including a folding optical system and a movable unit. Specifically, the optical path length of the laser beam 130 traveling from the light source 104 to the generating unit 101 is adjusted by interposing the optical delay unit 103 between the light source 104 and the generating unit 101.

Alternatively, the optical path length of the laser beam 130 inputted to the detecting unit 102 may be changed by positioning the optical delay unit 103 in a path along which the laser beam 130 is inputted to the detecting unit 102.

The scanning stage 109 changes the point of application of the terahertz wave 210 to the specimen 111. In the first embodiment, the scanning stage 109 holds the plate-like member 110, the specimen 111, and the reflecting member 112. The plate-like member 110, the specimen 111, and the reflecting member 112 move with the movement of the scanning stage 109, whereby the point of application of the terahertz wave 210 is changed. The point of application may be changed in any other way as long as the position of the set of the plate-like member 110, the specimen 111, and the reflecting member 112 relative to the position of the applying unit 117 can be changed.

Other details of the apparatus 100 will now be described. The apparatus 100 includes a computer including a central processing unit (CPU), a memory, a storage device, and so forth. The computer includes the control unit 105, the waveform acquiring unit 106, the information acquiring unit 107, the image forming unit 108, the storage unit 119, and other functions.

The control unit 105 controls the devices included in the measuring mechanism 120. For example, the control unit 105 controls the optical delay unit 103. The control unit 105 also controls the scanning stage 109 such that when the construction of a temporal waveform at a point of application is complete, the scanning stage 109 is moved so that the terahertz wave 210 is applied to another point.

The waveform acquiring unit 106 acquires the temporal waveform of the terahertz wave 215 on the basis of the amount of adjustment made by the optical delay unit 103 and the output from the detecting unit 102.

The information acquiring unit 107 acquires information on the specimen 111 that is obtained at each of different points of application. In the first embodiment, optical characteristics of the specimen 111 are obtained by using at least portions of the temporal waveform that represent terahertz waves 211, 212, and 213 reflected by the plate-like member 110, the specimen 111, and the reflecting member 112, respectively, the temporal waveform having been acquired by the waveform acquiring unit 106. The method of acquiring the information will be described separately below.

The image forming unit 108 forms an image by using the following pieces of information: position information on the point of application of the terahertz wave 210, the point of application being changed by moving the scanning stage 109; and optical characteristics of the specimen 111 at different points of application. The image thus formed can be displayed on a display unit (not illustrated) connected to the image forming unit 108.

The storage unit 119 stores the results of detection performed by the detecting unit 102, the temporal waveform representing the terahertz wave 215 acquired by the waveform acquiring unit 106, the information on the specimen 111 acquired by the information acquiring unit 107, the image formed by the image forming unit 108, and so forth. The storage unit 119 further stores programs corresponding to steps of a flowchart illustrated in FIG. 3. The CPU reads the programs and executes the programs, whereby the steps are performed. The steps illustrated in FIG. 3 will be described separately below.

The plate-like member 110 and the reflecting member 112 will now be described in detail. The plate-like member 110 is made of a material that is highly transmissive with respect to the terahertz wave 210. Desirable examples of the material include, but are not limited to, crystal that is cut along a z face, sapphire, high-resistivity silicon, cycloolefin polymer, tetrafluoroethylene, and polyethylene.

The plate-like member 110 is made of a material whose complex refractive index spectrum is known. The complex refractive index spectrum may be a typical value given in related literature, or may be measured in advance by a transmission THz-TDS method or the like. The measurement of the complex refractive index spectrum is desirably performed prior to the measurement of the specimen 111.

The reflecting member 112 has a reflecting surface 204 that reflects the terahertz wave 210. The reflecting surface 204 is made of a conductive member. The conductive member desirably has a reflectance spectrum $R_C$ obtained with the terahertz wave 210 that is perpendicularly incident thereon of 90% or higher than the reflectance spectrum obtained with any terahertz wave 210 applied to the specimen 111, regardless of the refractive index of the specimen 111. The reflectance spectrum $R_C$ is more desirably as close to 100% as possible.

Specifically, the material of the conductive member may be metal such as gold, silver, or aluminum; a semiconductor doped with impurities; liquid metal such as mercury; or the like. Alternatively, the reflecting member 112 itself may contain the foregoing material, or a conductive film containing the foregoing material may be provided on a surface of a flat plate-like substrate. The film can be formed by vacuum deposition or the like. Moreover, the terahertz wave 210 may be obliquely applied to the specimen 111 so that the terahertz wave 210 is totally reflected by the interface between the reflecting member 112 and the specimen 111. The specimen 111 is positioned on the reflecting surface 204 of the reflecting member 112.

Figure 2A:
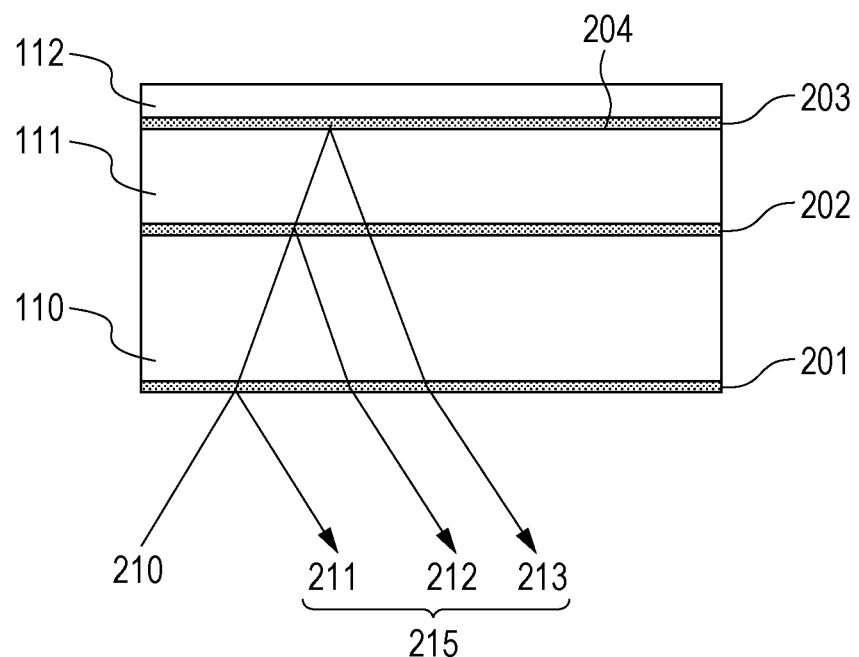
FIG. 2A is a schematic diagram illustrating terahertz wave applied to a specimen in the first embodiment.

A method of acquiring information on the specimen 111 by using the temporal waveform representing the terahertz wave 215 that have been acquired by the above method will now be described in detail with reference to FIGS. 2A and 2B. The first embodiment is based on an assumption that the complex refractive index spectrum of the plate-like member 110 and the thickness of the specimen 111 at each point of application are known. A case where the thickness of the specimen 111 is unknown will be described separately below in another embodiment.

First, how the terahertz wave 210 is reflected in the measurement of the specimen 111 performed by the information acquiring apparatus 100 according to the first embodiment will be described. FIG. 2A schematically illustrates how the terahertz wave 210 behaves when applied to the specimen 111. FIG. 2B is a chart illustrating a temporal waveform of the terahertz wave 215 as the reflection from the specimen 111. Herein, as a matter of simplicity, the terahertz wave 210 is assumed to be perpendicularly incident on the plate-like member 110, and the angle of incidence, the polarization, and the multiple reflection of the terahertz wave 210 in the plate-like member 110 and in the specimen 111 are ignored. Note that the angle of incidence of the terahertz wave 210 on the plate-like member 110 needs to be at least within a range in which the terahertz wave 210 that is incident is not totally reflected by an interface 201 and by an interface 202.

A portion of the terahertz wave 210 applied to the specimen 111 through the plate-like member 110 is reflected by the front surface of the plate-like member 110 (by the interface 201), whereby a reflected pulse A (corresponding to the terahertz wave 211) is obtained.

Another portion of the terahertz wave 210 that has passed through the interface 201 travels through the plate-like member 110 and is reflected by the interface 202 between the plate-like member 110 and the specimen 111, whereby a reflected pulse B (corresponding to the terahertz wave 212) is obtained. Here, the front surface of the plate-like member 110 corresponds to a surface on which the terahertz wave 210 emitted from the applying unit 117 is firstly incident. Another surface of the plate-like member 110 that is opposite the front surface is defined as the back surface. This also applies to the specimen 111 and to the reflecting member 112.

Yet another portion of the terahertz wave 210 that has passed through the interface 202 travels through the specimen 111 while being absorbed by the specimen 111, and is reflected by an interface 203 between the specimen 111 and the reflecting surface 204 of the reflecting member 112 at a high reflectance, whereby a reflected pulse C (corresponding to the terahertz wave 213) is obtained. Each of the reflected pulses A to C (211 to 213) reaches the detecting unit 102 and is thus detected by the detecting unit 102.

Note that the following description is based on an assumption that even in the case where a matching liquid is interposed between the plate-like member 110 and the specimen 111 or between the specimen 111 and the reflecting member 112, the plate-like member 110 and the specimen 111 define the interface 202 and the specimen 111 and the reflecting surface 204 of the reflecting member 112 define the interface 203.

It is desirable that a confocal mechanism that is capable of focusing the terahertz wave 210 generated by the generating unit 101 on any position be provided for improving the accuracy in the measurement of the temporal waveform. Alternatively, it is desirable that the length from the front surface of the plate-like member 110 (the interface 201) to the back surface of the reflecting member 112 fall within a range corresponding to the depth of focus of the terahertz wave 210.

The waveform acquiring unit 106 acquires a temporal waveform by using the results of the detection performed by the detecting unit 102. The temporal waveform thus acquired is illustrated in FIG. 2B. The reflected pulses A to C (211 to 213) detected by the detecting unit 102 occur with time delays in accordance with the distances by which the terahertz waves 210 and 215 travel through any of the elements and the refractive indices of those elements through which the terahertz waves 210 and 215 travel. Therefore, as illustrated in FIG. 2B, the reflected pulses A to C (211 to 213) are detected by the detecting unit 102 at respectively different points of time.

Now, how the information acquiring unit 107 acquires information on the specimen 111 from the temporal waveform acquired as described above will be described.

Figure 2B:
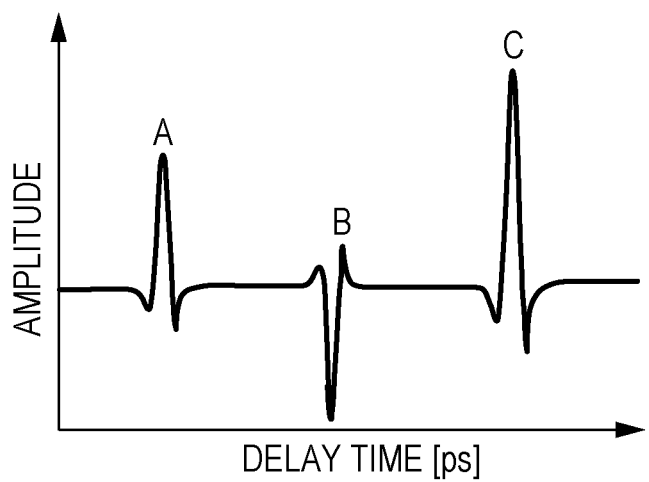
FIG. 2B is a chart illustrating a temporal waveform according to the first embodiment.

The waveform acquiring unit 106 acquires a temporal waveform containing the reflected pulses A, B, and C (211, 212, and 213), illustrated in FIG. 2B, from the results of the detection of the terahertz wave 215 that is performed by the detecting unit 102. The temporal waveform thus acquired is output to the information acquiring unit 107. The information acquiring unit 107 separates the temporal waveform representing the terahertz wave 215 into portions that correspond to the respective reflected pulses A, B, and C (211, 212, and 213). The separated portions are each subjected to Fourier transformation. Thus, amplitude spectra of the respective portions are obtained. Then, the amplitude spectra are each squared, whereby intensity spectra of the respective portions are obtained.

The thickness of the plate-like member 110 may be adjusted so that the information acquiring unit 107 can easily perform the separation of the reflected pulse A (211) and the reflected pulse B (212) produced at the interface 201 and the interface 202, respectively. For example, in a case where the reflected pulse A (211) and the reflected pulse B (212) each have a pulse width of 300 fs, the time difference between the two can be set to 1 ps or larger so that the two are not superposed on each other on the temporal waveform. That is, in the case where the terahertz wave 210 is applied perpendicularly, if the refractive index of the plate-like member 110 is 2, the thickness of the plate-like member 110 can be set to 75 μm or larger.

In the case where the temporal waveform is subjected to Fourier transformation for acquiring the information on the specimen 111, the frequency resolution increases with the length of each of the separated portions of the temporal waveform along the time axis. That it, as the thickness of the plate-like member 110 increases, the interval between the reflected pulses A to C (211 to 213) in the temporal waveform increases. Therefore, the temporal waveform can be separated into portions each containing a long time domain. Thus, the frequency resolution is improved by performing Fourier transformation.

Letting the intensity spectrum of the terahertz wave (input pulse) 210 be $I_1$, and the intensity spectra of the reflected pulses A, B, and C (211, 212, and 213) be $I_A$, $I_B$, and $I_C$, the following expressions are established:

$$I_A = R_A I_1 \quad (1)$$

$$I_B = R_B(1-R_A)^2 \exp(-2\alpha_w d_{w1}) I_1 \quad (2)$$

$$I_C = R_C(1-R_B)^2(1-R_A)^2 \exp(-2\alpha_w d_{w1})\exp(-2\alpha_{sam} d_{sam}) I_1 \quad (3)$$

where $R_A$, $R_B$, and $R_C$ denotes the reflectance spectra at the respective interfaces 201, 202, and 203; $\alpha_w$ denotes the absorption coefficient spectrum of the plate-like member 110; $d_{w1}$ denotes the thickness of the plate-like member 110; $\alpha_{sam}$ denotes the absorption coefficient spectrum of the specimen 111; and $d_{sam}$ denotes the thickness of the specimen 111.

The reflectance spectra $R_A$, $R_B$, and $R_C$ in Expressions (1) to (3) are represented by the following expressions, respectively, by using the complex refractive index spectra of the substances constituting the respective interfaces 201, 202, and 203:

$$R_A = \frac{(n_w - 1)^2 + \kappa_w^2}{(n_w + 1)^2 + \kappa_w^2} \quad (4)$$

$$R_B = \frac{(n_{sam} - n_w)^2 + (\kappa_{sam} - \kappa_w)^2}{(n_{sam} + n_w)^2 + (\kappa_{sam} + \kappa_w)^2} \quad (5)$$

$$R_C = \frac{(n_m - n_{sam})^2 + (\kappa_m - \kappa_{sam})^2}{(n_m + n_{sam})^2 + (\kappa_m + \kappa_{sam})^2} \cong 1 \quad (6)$$

where $n_w$, $n_{sam}$, and $n_m$ denote the real parts (refractive index spectra) of the complex refractive index spectra of the plate-like member 110, the specimen 111, and the reflecting surface 204 of the reflecting member 112, respectively; and $\kappa_w$, $\kappa_{sam}$, and $\kappa_m$ denote the imaginary parts (extinction coefficient spectra) of the complex refractive index spectra of the plate-like member 110, the specimen 111, and the reflecting surface 204 of the reflecting member 112, respectively.

The refractive index spectrum $n_m$ and the extinction coefficient spectrum $\kappa_m$ of the reflecting surface 204 of the reflecting member 112 are much larger than the refractive index spectrum $n_{sam}$ and the extinction coefficient spectrum $\kappa_{sam}$, respectively, of the specimen 111. Therefore, the reflectance spectrum $R_C$ can be regarded as a constant value that is close to 1, regardless of the complex refractive index spectrum of the specimen 111.

On the basis of Expressions (1) and (2), the reflectance spectrum $R_B$ at the interface 202 between the plate-like member 110 and the specimen 111 is represented by Expression (7):

$$R_B = \frac{R_A}{(1-R_A)^2} \exp(2\alpha_w d_{w1}) \frac{I_B}{I_A} \quad (7)$$

where $R_A$ denotes the reflectance spectrum at the interface 201, $\alpha_w$ denotes the absorption coefficient spectrum of the plate-like member 110, and $d_{w1}$ denotes the thickness of the plate-like member 110.

If the reflectance spectrum $R_A$ at the interface 201, the absorption coefficient spectrum $\alpha_w$ of the plate-like member 110, and the thickness $d_{w1}$ of the plate-like member 110 are determined from Expression (7), the reflectance spectrum $R_B$ at the interface 202 can be obtained. Furthermore, Expression (8) is derived from Expressions (2) and (3):

$$\alpha_{sam} = \frac{4\pi f}{c}\kappa_{sam} = -\frac{1}{2d_{sam}}\ln\left\{\frac{I_C}{I_B} \times \frac{R_B}{(1-R_B)^2}\right\} \quad (8)$$

where c denotes the speed of light, and f denotes the frequency. According to Expression (8), if the thickness $d_{sam}$ of the specimen 111 is known and the reflectance spectrum $R_B$ is determined, the absorption coefficient spectrum $\alpha_{sam}$ of the specimen 111 can be obtained.

If the absorption coefficient spectrum $\alpha_{sam}$ of the specimen 111 is determined, the extinction coefficient spectrum $\kappa_{sam}$ of the specimen 111 can be obtained from Expression (8). Furthermore, the refractive index spectrum $n_{sam}$ of the specimen 111 can be obtained from Expression (5).

Furthermore, a set of a dielectric constant spectrum $\in_1$ as the real part and a dielectric loss spectrum $\in_2$ as the imaginary part of the complex dielectric constant spectrum of the specimen 111 and a set of the refractive index spectrum $n_{sam}$ as the real part and the extinction coefficient spectrum $\kappa_{sam}$ as the imaginary part of the complex refractive index spectrum are in a relationship represented by Expression (9):

$$\tilde{\in} = \in_1 + i\in_2 = (n_{sam} + i\kappa_{sam})^2$$

$$\in_1 = n_{sam}^2 - \kappa_{sam}^2 \quad \in_2 = 2n_{sam}\kappa_{sam} \quad (9)$$

According to Expression (9), a complex dielectric constant spectrum $\tilde{\in}$ of the specimen 111 can be obtained.

Here, the thickness of the specimen 111 needs to be large enough to allow the separation of the reflected pulse B (212) and the reflected pulse C (213) on the temporal waveform and to be within a range in which the reflected pulse C (213) having traveled through the specimen 111 can be acquired as a signal. Therefore, the thickness of the specimen 111 is desirably within a range defined by Expression (10):

$$\frac{c\Delta t}{2n_{sam}} \le d_{sam} \le \frac{1}{2\alpha_{sam}}\ln(SNR) \quad (10)$$

where c denotes the speed of light, $\Delta t$ denotes the pulse width of the terahertz wave 210, and SNR denotes the signal-to-noise (S/N) ratio of the intensity of the terahertz wave 210.

To define the thickness of the specimen 111, a space is provided between the plate-like member 110 and the reflecting member 112 by interposing a member having a uniform height or a plurality of members having the same height, and the specimen 111 is put into the space. Thus, the specimen 111 is provided in contact with the plate-like member 110 and with the reflecting member 112. Hence, the height of the member/members is regarded as the thickness of the specimen 111. The thickness of the specimen 111 may be defined in any other way and is not limited. For example, the specimen 111 may be put into a case (not illustrated) whose height is known, and the case may be held between the plate-like member 110 and the reflecting member 112. The thickness of the specimen 111 thus obtained is stored in the storage unit 119 and is output to the information acquiring unit 107, according to need.

As described above, in the case where the thickness $d_{sam}$ of the specimen 111 is known, if the thickness $d_{w1}$ of the plate-like member 110 is determined, the information acquiring unit 107 can acquire the reflectance spectrum $R_B$ at the interface 202 from Expression (7). Consequently, optical characteristics of the specimen 111 can be obtained.

Figure 3:
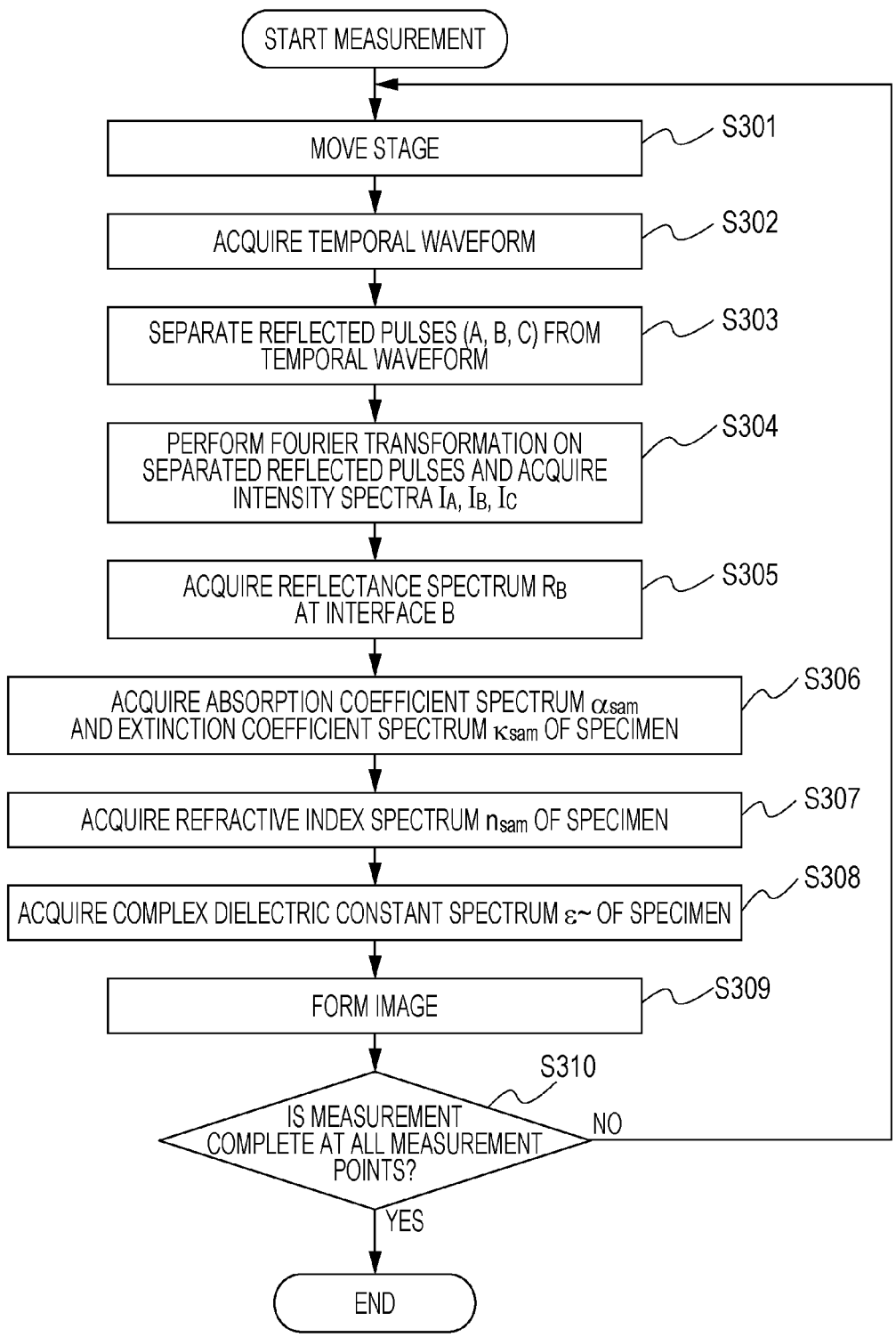
FIG. 3 is a flowchart illustrating an information acquiring method according to the first embodiment.

Now, an influence brought upon the measurement accuracy by the thickness $d_{w1}$ of the plate-like member 110 will be described. The following description concerns an exemplary case where the thickness of the plate-like member 110 at one arbitrary point is measured by using a micrometer or the like, and the measured value is substituted for $d_{w1}$ in Expression (7). FIG. 3 is a flowchart illustrating steps of acquiring optical characteristics of the specimen 111.

When the apparatus 100 starts measurement, the control unit 105 sends a command to the scanning stage 109, whereby the scanning stage 109 is moved to a position where the terahertz wave 210 is to be applied to the specimen 111 (S301). Subsequently, the applying unit 117 applies the terahertz wave 210 to the specimen 111 through the plate-like member 110, and the terahertz wave 215 containing the reflected pulses A, B, and C (211, 212, and 213) is detected by the detecting unit 102. The waveform acquiring unit 106 acquires a temporal waveform from the results of the detection performed by the detecting unit 102 (S302). The information acquiring unit 107 then separates portions of the acquired temporal waveform that correspond to the respective reflected pulses A, B, and C (211, 212, and 213) from the temporal waveform (S303). The information acquiring unit 107 then performs Fourier transformation on each of the separated portions, thereby acquiring the intensity spectra $I_A$, $I_B$, and $I_C$ (S304).

Subsequently, the information acquiring unit 107 acquires the reflectance spectrum $R_B$ at the interface 202 from Expression (7) (S305). The information acquiring unit 107 further acquires the information on the thickness $d_{sam}$ of the specimen 111 from the storage unit 119, and calculates the absorption coefficient spectrum $\alpha_{sam}$ of the specimen 111 and the extinction coefficient spectrum $\kappa_{sam}$ of the specimen 111 from Expression (8) (S306). The information acquiring unit 107 further calculates the refractive index spectrum $n_{sam}$ of the specimen 111 from Expression (5) (S307), and then calculates the complex dielectric constant spectrum $\tilde{\in}$ of the specimen 111 from Expression (9) (S308).

The optical characteristics of the specimen 111 acquired as described above are transferred to the image forming unit 108 in association with the position information on the point of application, and the image forming unit 108 forms an image by using the position information on the point of application and the optical characteristics of the specimen 111 (S309). When the image formation is complete, whether or not the measurement is complete at all points in a measurement area is checked (S310). If not, the process returns to step S301, in which the scanning stage 109 is moved and a temporal waveform at another measurement point is acquired. If temporal waveforms at all measurement points have been acquired, the apparatus 100 ends the measurement.

The first embodiment concerns a case where whether or not the measurement is complete at all points is checked after an image is formed by the image forming unit 108. The present invention is not limited to such a case. The acquisition of information on the specimen 111 in steps S303 to S308 may be performed simultaneously with the check performed in step S310 and the moving of the scanning stage 109. Specifically, after acquiring a temporal waveform in step S302, the information acquiring unit 107 acquires information on the specimen 111 by using the acquired temporal waveform. Simultaneously, the control unit 105 receives a signal representing the completion of acquisition of the temporal waveform, and, if necessary, sends a command to the scanning stage 109 so that the point of application is changed. In such a configuration, the acquisition of optical characteristics of the specimen 111 by the information acquiring unit 107, the changing of the measurement point, and the measurement of the temporal waveform can all be performed simultaneously. Consequently, the measurement time is reduced.

As another alternative, which ones of the optical characteristics are necessary as the information on the specimen 111 may be preset, whereby the steps of acquiring optical characteristics other than the preset ones may be omitted. For example, if the refractive index spectrum $n_{sam}$ of the specimen 111 needs to be obtained, step S308 for calculating the complex dielectric constant spectrum $\mathcal{E}^{\sim}$ can be omitted. If the refractive index spectrum $n_{sam}$ of the specimen 111 needs to be obtained, an expression for calculating the refractive index spectrum $n_{sam}$ may be obtained in advance, whereby the refractive index spectrum $n_{sam}$ of the specimen 111 can be acquired without calculating the absorption coefficient spectrum $\alpha_{sam}$ and the extinction coefficient spectrum $\kappa_{sam}$.

The first embodiment concerns a case where an image is acquired by using pieces of information on the specimen 111 acquired at different measurement points defined by changing the point of application of the terahertz wave 210. Therefore, if the thickness of the plate-like member 110 is acquired only at one arbitrary point, the thickness of the plate-like member 110 at each point of application of the terahertz wave 210 might not be obtained correctly. That is, an error might occur. Moreover, there might be an error in the thickness of the plate-like member 110 that has been measured at the one arbitrary point.

Specifically, there is an error $\Delta d_w$ between the thickness $d_{w1}$ used in acquiring the reflectance spectrum $R_B$ at the interface 202 in step S305 and the actual thickness of the plate-like member 110 at each point of application. In other words, the length by which the terahertz wave 210 travels in the plate-like member 110 is longer than or shorter than the actual length by the error $\Delta d_w$.

Here, supposing that the absorption coefficient spectrum $\alpha_w$ of the plate-like member 110 is about 1 cm$^{-1}$ and an error of about 1% is allowable in terms of measurement accuracy, desired measurement accuracy is estimated to be satisfied if the error $\Delta d_w$ is smaller than about 50 µm. That is, if the error $\Delta d_w$ is smaller than about 50 µm, the influence brought by the error $\Delta d_w$ is represented by Expression (11):

$$\exp\{2\alpha_w(\Delta d_w)\} \cong 1 \quad (11)$$

In the known method, it is not easy to acquire information on the specimen 111 with high accuracy under the same conditions as described above even if the error $\Delta d_w$ is about 1 µm. In contrast, in the first embodiment, a wide allowance is provided for the error $\Delta d_w$. Hence, there is no need to highly accurately know the thickness of the plate-like member 110.

The tolerance on the parallelism of the plate-like member 110 manufactured by cutting performed with a standard machine tool is about 10 µm, which is smaller than the above allowable error of about 50 µm. Hence, the influence of an error in the thickness of the plate-like member 110 upon the measurement accuracy is small. Therefore, if the parallelism of the plate-like member 110 is based on the measurement accuracy provided in a standard machining process, there is no need to acquire the thickness of the plate-like member 110 at each of all points of application with high accuracy.

The apparatus 100 acquires information on the specimen 111 by using the intensity spectra $I_B$ and $I_C$ acquired from the temporal waveform representing a portion of the terahertz wave 210 that has been reflected by the interface 202 between the plate-like member 110 and the specimen 111 and the temporal waveform representing a portion of the terahertz wave 210 that has been reflected by the interface 203 between the specimen 111 and the reflecting member 112, respectively. The reflectance spectrum $R_B$ at the interface 202 between the plate-like member 110 and the specimen 111 is obtained from the amount of attenuation in the intensity of the terahertz wave 210 traveling through the specimen 111 and from the thickness of the specimen 111. The amount of attenuation in the intensity of the terahertz wave 210 is obtained from the intensity spectra $I_B$ and $I_C$. Therefore, information on the specimen 111 can be acquired by using the reflectance spectrum $R_B$. That is, optical characteristics of the specimen 111 can be acquired without using the amount of change in the phase of the terahertz wave 210 that occurs while the terahertz wave 210 travels through the plate-like member 110. Hence, the influence brought by the thickness of the plate-like member 110 is smaller than that in the case where optical characteristics of the specimen 111 are acquired by using the amount of change in the phase at the interface 202 between the plate-like member 110 and the specimen 111. Therefore, even if the thickness of the plate-like member 110 is not uniform, highly accurate measurement can be performed.

Second Embodiment

Figure 4A:
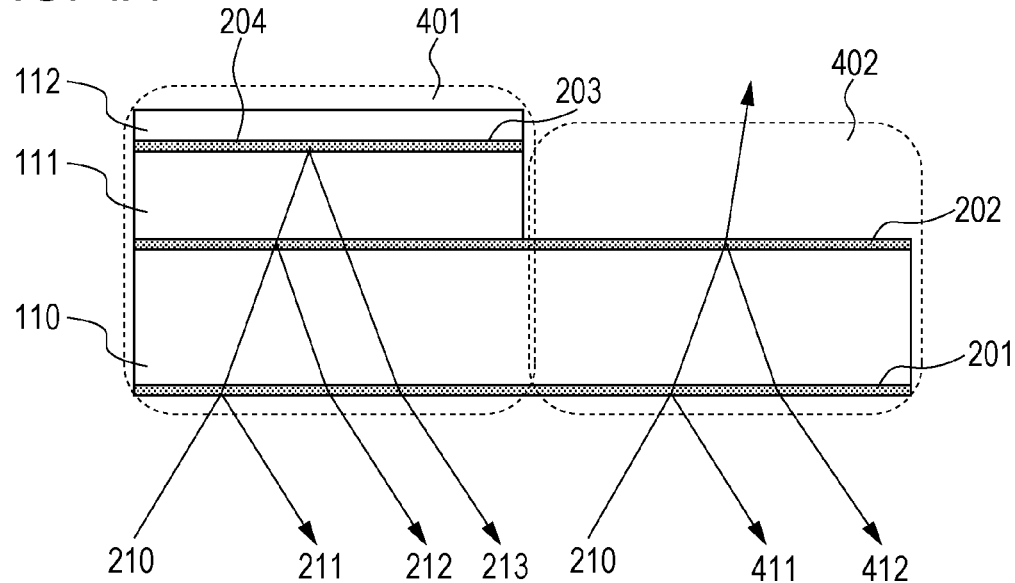
FIG. 4A illustrates a plate-like member according to a second embodiment.

An information acquiring apparatus according to a second embodiment will now be described. Description of details that are common to those described above is omitted. The information acquiring apparatus according to the second embodiment has the same configuration as in the first embodiment, but the method of acquiring information on the specimen 111 is different from that of the first embodiment. Specifically, the storage unit 119 according to the second embodiment stores programs corresponding to steps of a flowchart illustrated in FIG. 5. The CPU reads the programs and executes the programs, whereby the steps are performed. FIG. 4A is an enlarged view of the specimen 111 and associated elements.

As illustrated in FIG. 4A, the plate-like member 110 according to the second embodiment includes a specimen-present area 401 in which the specimen 111 is present between the plate-like member 110 and the reflecting member 112, and a specimen-less area 402 in which the reflecting member 112 and the specimen 111 are absent. It is desirable to measure not only the reflected pulses A, B, and C (211, 212, and 213) obtained by applying the terahertz wave 210 to the specimen-present area 401 but also reflected pulses D and E (411 and 412) obtained by applying the terahertz wave 210 to the specimen-less area 402. The reflected pulses D and E (411 and 412) are the reflections from the interface 201 and the interface 202, respectively. In such a case, the reflected pulses D and E (411 and 412) only need to be measured at least once: before, after, or during the measurement of the specimen-present area 401, or at any other like timing.

While FIG. 4A illustrates an exemplary case where no substance but air is provided on the back surface of the plate-like member 110 in the specimen-less area 402, any substance, other than air, whose complex refractive index spectrum is known may be provided on the back surface of the plate-like member 110 in the specimen-less area 402. Moreover, the reflecting member 112 may extend over the specimen-less area 402 so that the interface 203 is provided. In that case, air or any substance whose complex refractive index spectrum is known may be provided between the plate-like member 110 and the reflecting member 112.

In such a configuration, even if the specimen 111 is a substance, such as a living body, whose optical characteristics change when water contained therein evaporates, the drying of the specimen 111 can be prevented by filling the specimen-less area 402 with oil or the like.

Figure 5:
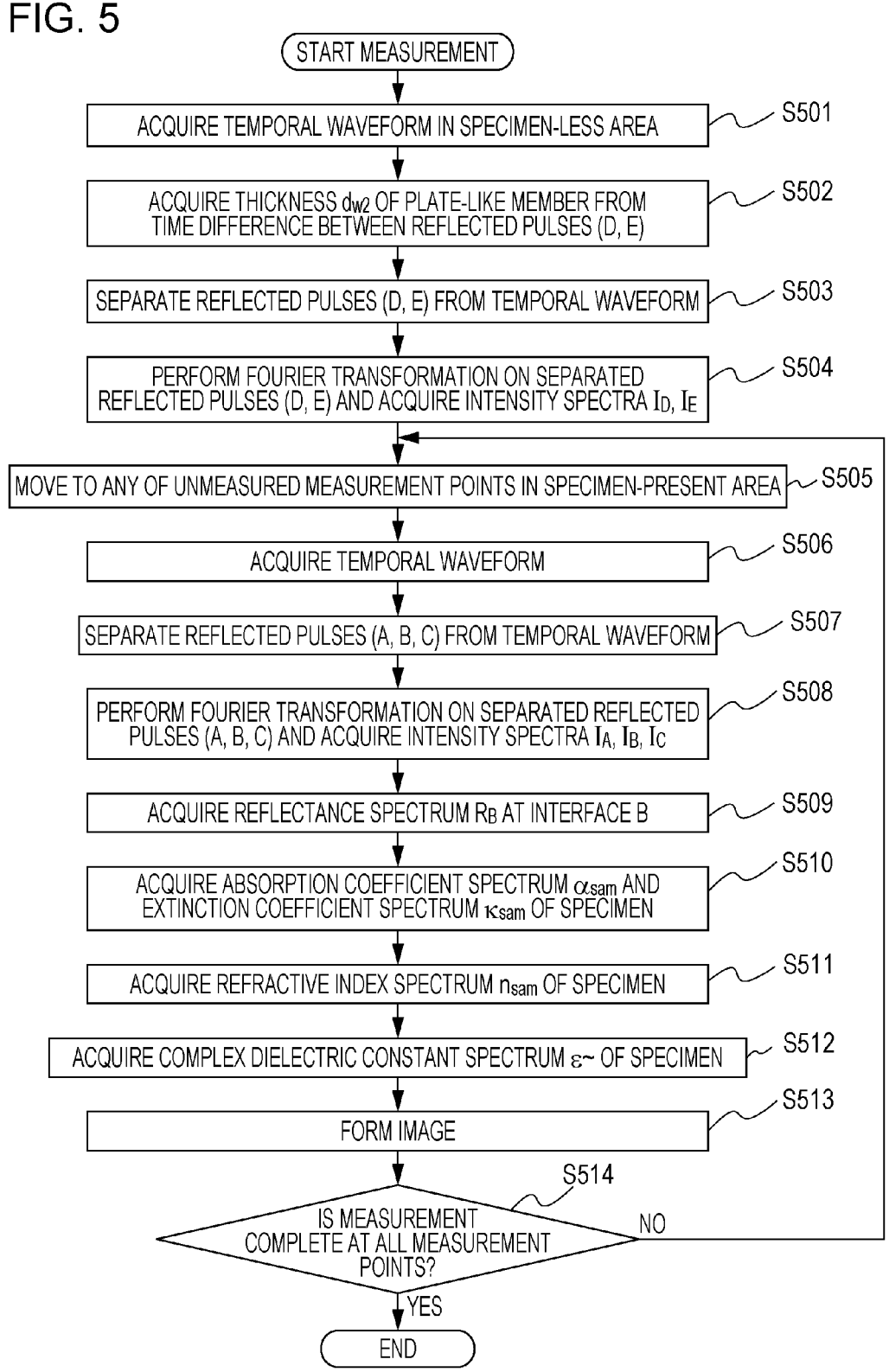
FIG. 5 is a flowchart illustrating an information acquiring method according to the second embodiment.

FIG. 5 is a flowchart illustrating steps of acquiring optical characteristics of the specimen 111 in the second embodiment.

In the second embodiment, a temporal waveform is acquired by first applying the terahertz wave 210 to the specimen-less area 402 (S501). Subsequently, a thickness $d_{w2}$ of the plate-like member 110 in the specimen-less area 402 is calculated in accordance with Expression (12) below using a time difference $t_{DE}$ between the time when the reflected pulse D (411) is detected and the time when the reflected pulse E (412) is detected (S502).

$$d_{w2} = \frac{ct_{DE}}{2n_w} \tag{12}$$

Regarding the acquisition of the time of detection of each of the reflected pulses D and E (411 and 412) and the acquisition of the time difference between the reflected pulses D and E (411 and 412), there are many known methods for accurately calculating the peak position and peak interval. Namely, deconvolution, a method in which a curve that best represents the waveform is obtained by regression, a method in which Fourier transformation is performed on a peak waveform and the change in phase that occurs with time is checked, and so forth. An appropriate one of such methods is selected in accordance with the situation. Herein, the time difference $t_{DE}$ is obtained simply on the basis of the points of time when the peak values of the temporal waveform that correspond to the respective reflected pulses D and E (411 and 412) are detected.

Subsequently, the reflected pulses D and E (411 and 412) are separated from the temporal waveform (S503). Then, Fourier transformation is performed on each of the reflected pulses D and E (411 and 412), whereby amplitude spectra of the respective reflected pulses D and E (411 and 412) are obtained. Then, the amplitude spectra of the reflected pulses D and E (411 and 412) are each squared, whereby intensity spectra $I_D$ and $I_E$ are obtained (S504).

Here, letting the intensity of the terahertz wave 210 be $I_2$, Expressions (13) and (14) are established:

$$I_D = R_A I_2 \tag{13}$$

$$I_E = R_A(1-R_A)^2 \exp(-2\alpha_w d_{w2}) I_2 \tag{14}$$

When the measurement of the specimen-less area 402 is complete, the control unit 105 moves the scanning stage 109 to a position where the terahertz wave 210 is applied to a point in the specimen-present area 401 (S505). Then, the terahertz wave 210 is applied from the applying unit 117 to the measurement point in the specimen-present area 401, and the detecting unit 102 detects the terahertz wave 215. The waveform acquiring unit 106 acquires a temporal waveform from the results of detection by the detecting unit 102 (S506).

If the number of times of calculation is increased for higher measurement accuracy, the intensity of the terahertz wave 210 may vary between that in the measurement of the specimen-present area 401 and that in the measurement of the specimen-less area 402. Hence, in the second embodiment, it is assumed that intensities $I_1$ and $I_2$ of the terahertz wave 210 are different. Even in such a case, if the intensity spectra $I_D$ and $I_E$ of the reflected pulses D and E (411 and 412) are acquired, the reflectance spectrum $R_B$ at the interface 202 in which the variation in the intensity of the terahertz wave 210 is cancelled out can be obtained. The reflectance spectrum $R_B$ is represented by Expression (15) below that is based on Expressions (1), (2), (13), and (14):

$$R_B = R_A \exp\{2\alpha_w(d_{w1} - d_{w2})\}\frac{I_B \times I_D}{I_A \times I_E} \tag{15}$$

The plate-like member 110 is made of a material that is highly transmissive with respect to the terahertz wave 210 and whose absorption coefficient spectrum $\alpha_w$ is about 1 cm$^{-1}$. If an error of about 1% is allowable in terms of measurement accuracy, a difference of up to about 50 µm between the thickness $d_{w1}$ of the plate-like member 110 in the specimen-present area 401 and the thickness $d_{w2}$ of the plate-like member 110 in the specimen-less area 402 is ignorable, as in the first embodiment. That is, the effect of absorption of the terahertz wave 210 by the plate-like member 110 that is represented on the right side of Expression (15) is regarded as Expression (16) below:

$$\exp\{2\alpha_w(d_w-d_w')\} \cong 1 \tag{16}$$

Therefore, as in the first embodiment, if the plate-like member 110 is manufactured with accuracy obtained in a standard machining process, the influence of the thickness of the plate-like member 110 upon the accuracy in the acquisition of information on the specimen 111 is small. Therefore, the influence of the difference in the thickness of the plate-like member 110 upon the measurement accuracy is far smaller than that in the case where information on the specimen 111 is acquired by the method disclosed by Japanese Patent Laid-Open No. 2011-112548. Hence, the information acquiring unit 107 acquires the reflectance spectrum $R_B$ by using Expressions (15) and (16) (S509).

Subsequently, as in the first embodiment, the information acquiring unit 107 calculates the absorption coefficient spectrum $\alpha_{sam}$ and the extinction coefficient spectrum $\kappa_{sam}$ of the specimen 111 by using the reflectance spectrum $R_B$ acquired as described above (S510). Furthermore, the information acquiring unit 107 acquires the refractive index spectrum $n_{sam}$ and the complex dielectric constant spectrum $\in^\sim$ of the specimen 111 (S511 and S512). Subsequently, the image forming unit 108 forms an image on the basis of the optical characteristics acquired as described above (S513). Then, the control unit 105 checks whether or not the measurement is complete at all measurement points (S514). If not, the process returns to step S505, and the above series of steps are performed again.

As described above, in the apparatus 100 according to the second embodiment, the reflectance spectrum $R_B$ at the interface 202 between the plate-like member 110 and the specimen 111 is obtained from the thickness of the specimen 111 and the amount of attenuation in the intensity of the terahertz wave 210 traveling through the specimen 111. Thus, information on the specimen 111 can be acquired by using the reflectance spectrum $R_B$. That is, optical characteristics of the specimen 111 can be acquired without using the amount of change in the phase of the terahertz wave 210 that occurs while the terahertz wave 210 travels through the plate-like member 110.

Even if the thickness of the plate-like member 110 is unknown, information on the specimen 111 can be acquired by obtaining the thickness of the plate-like member 110 from the temporal waveform obtained by at least one measurement of the specimen-less area 402. In this case, if the parallelism of the plate-like member 110 has only an error that may occur in a standard machining process, information on the specimen 111 can be acquired with high accuracy even if the thickness of the plate-like member 110 varies with the point of application of the terahertz wave 210.

In the second embodiment, the information acquiring unit 107 obtains the reflectance spectrum $R_B$ by using Expression (15). Alternatively, after the thickness of the plate-like member 110 is obtained by using Expression (12), the reflectance spectrum $R_B$ may be obtained by using Expression (7) used in the first embodiment.

Third Embodiment

A method of acquiring information on the specimen 111 according to a third embodiment will now be described in which the thickness of the specimen 111 is unknown. An information acquiring apparatus according to the third embodiment has the same configuration as the apparatus 100 according to the first embodiment. The storage unit 119 of the apparatus 100 according to the third embodiment stores programs corresponding to steps of a flowchart illustrated in FIG. 6. The CPU reads the programs and executes the programs, whereby the steps are performed.

Figure 6:
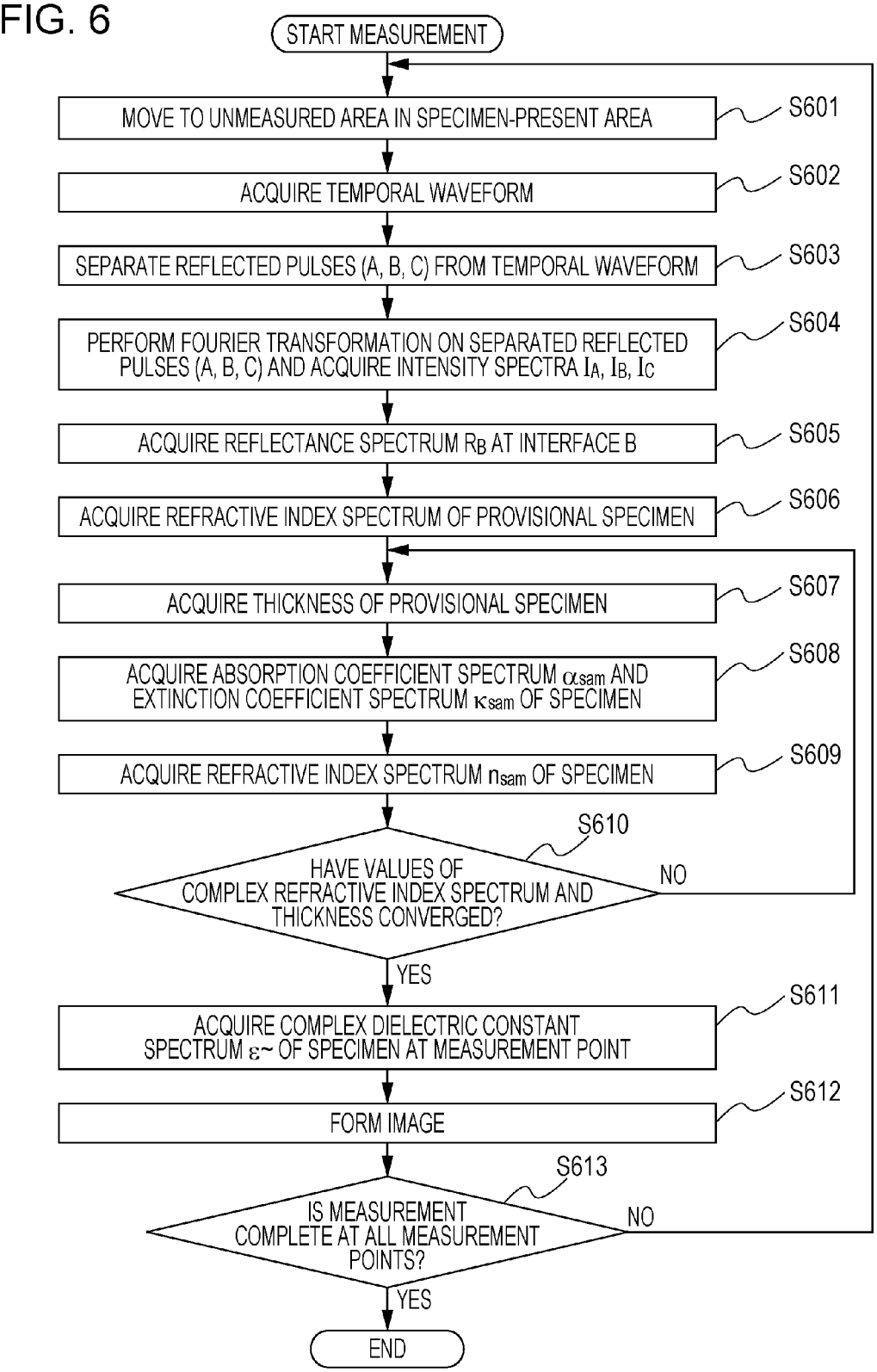
FIG. 6 is a flowchart illustrating an information acquiring method according to a third embodiment.

FIG. 6 is a flowchart illustrating steps of acquiring optical characteristics of the specimen 111 in the third embodiment. In FIG. 6, the process up to the acquisition of the reflectance spectrum $R_B$ (S601 to S605) is the same as that of the first embodiment, and description thereof is therefore omitted. After the reflectance spectrum $R_B$ is acquired in step S605, the information acquiring unit 107 assumes that the specimen 111 is a provisional specimen 111 that does not absorb the terahertz wave 210, that is, a provisional specimen 111 having an extinction coefficient of zero. Then, the information acquiring unit 107 obtains the refractive index spectrum of the provisional specimen 111 in accordance with Expression (5) (S606). Subsequently, the information acquiring unit 107 acquires the thickness of the provisional specimen 111 from Expression (17) below by using the refractive index spectrum of the provisional specimen 111 and the time difference between the reflected pulses B and C (212 and 213) illustrated in FIG. 2B (S607). Expression (17) is as follows:

$$d_{sam} = \frac{ct_{BC}}{2n_{sam}} \quad (17)$$

where c denotes the speed of light, and $t_{BC}$ denotes the time difference between a portion of the temporal waveform that corresponds to the reflected pulse B (212) and a portion of the temporal waveform that corresponds to the reflected pulse C (213).

The information acquiring unit 107 then calculates the absorption coefficient spectrum $\alpha_{sam}$ and the extinction coefficient spectrum $\kappa_{sam}$ of the specimen 111 from Expression (8), as in the first embodiment, by using the thickness of the provisional specimen 111 (S608), and calculates the refractive index spectrum $n_{sam}$ of the specimen 111 again by using the extinction coefficient spectrum $\kappa_{sam}$ (S609). Furthermore, the provisional refractive index spectrum acquired in step S606 is substituted for by the refractive index spectrum $n_{sam}$ acquired in step S609, and the calculation is repeated until the values of the complex refractive index spectrum (the refractive index spectrum $n_{sam}$ and the extinction coefficient spectrum $\kappa_{sam}$) of the specimen 111 and the thickness of the specimen 111 converge.

When it has been confirmed that the values of the complex refractive index spectrum and the thickness of the specimen 111 have converged in step S610, the information acquiring unit 107 performs a process that corresponds to the process from steps S308 to S310 in the first embodiment, by using the converged complex refractive index spectrum and the converged thickness $d_{sam}$ of the specimen 111. Thus, the information acquiring unit 107 acquires the information on the specimen 111.

In the above configuration, the apparatus 100 can acquire optical characteristics of the specimen 111 without using the amount of change in the phase of the terahertz wave 210 that occurs while the terahertz wave 210 travels through the plate-like member 110. Even if the thickness of the specimen 111 at each point of application is unknown, the thickness of the specimen 111 and the information on the specimen 111 can be acquired by performing convergence calculation.

Fourth Embodiment

A method of acquiring information on the specimen 111 according to a fourth embodiment will now be described in which the thickness of the specimen 111 is unknown. The method according to the fourth embodiment is different from the method according to the third embodiment. Description of details that are common to those described above is omitted. An information acquiring apparatus according to the fourth embodiment has the same configuration as the apparatus 100 according to the first embodiment. The storage unit 119 of the apparatus 100 according to the fourth embodiment stores programs corresponding to steps of a flowchart illustrated in FIG. 7. The CPU reads the programs and executes the programs, whereby the steps are performed.

Figure 4B:
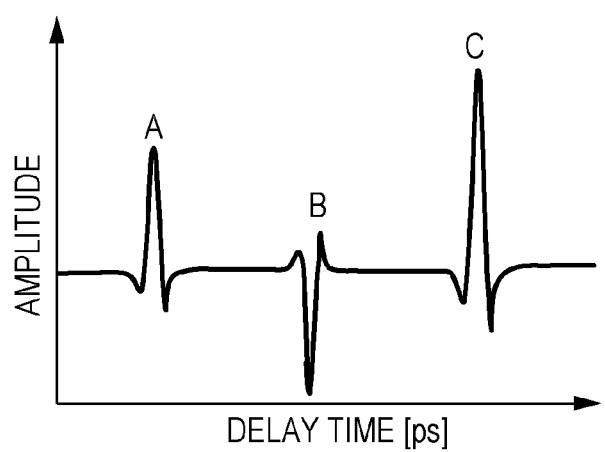
FIG. 4B is a chart illustrating a temporal waveform of terahertz wave applied to a specimen-present area according to the second embodiment.
Figure 4C:
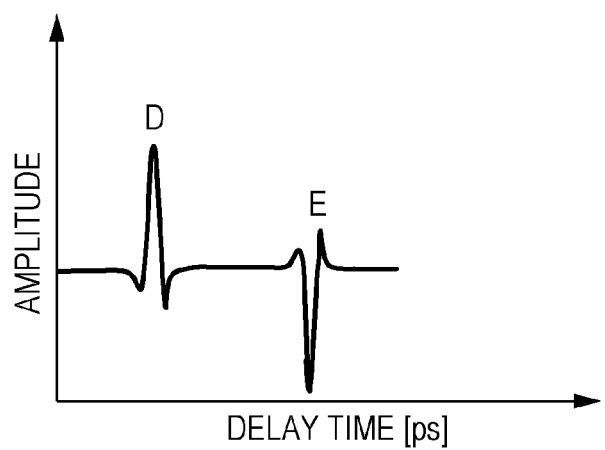
FIG. 4C is a chart illustrating a temporal waveform of the terahertz wave applied to a specimen-less area according to the second embodiment.

In the fourth embodiment, the plate-like member 110 includes a specimen-present area 401 and a specimen-less area 402, as in the second embodiment. The measuring mechanism 120 applies the terahertz wave 210 to the specimen-present area 401, whereby a temporal waveform representing the terahertz wave 215 containing the reflected pulses A to C (211 to 213) (see FIG. 4B) is acquired. The measuring mechanism 120 also applies the terahertz wave 210 to the specimen-less area 402, whereby a temporal waveform containing the reflected pulses D and E (411 and 412) (see FIG. 4C) is acquired. It is desirable to measure the reflected pulses D and E (411 and 412) at least once before the measurement of the specimen-present area 401 is performed.

Figure 7:
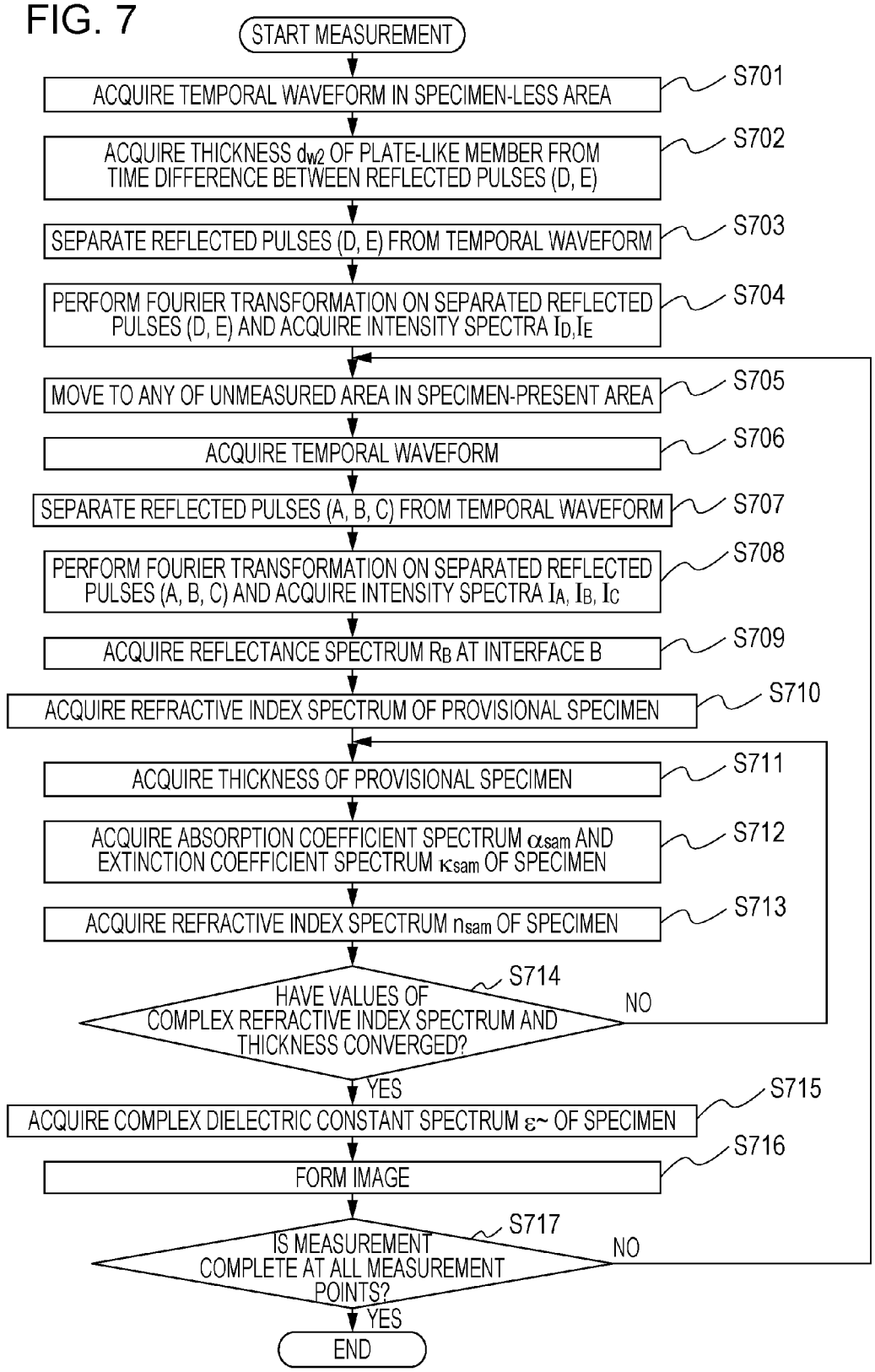
FIG. 7 is a flowchart illustrating an information acquiring method according to a fourth embodiment.

FIG. 7 is a flowchart illustrating steps of acquiring optical characteristics of the specimen 111 in the fourth embodiment. First, the reflectance spectrum $R_B$ at the interface 202 is acquired through the same process as in the second embodiment (S701 to 709).

Subsequently, the information acquiring unit 107 assumes that the specimen 111 is a provisional specimen 111 that does not absorb the terahertz wave 210, that is, a provisional specimen 111 having an extinction coefficient of zero, and the information acquiring unit 107 obtains the refractive index spectrum of the provisional specimen 111 in accordance with Expression (5) (S710). Subsequently, the information acquiring unit 107 acquires the thickness of the provisional specimen 111 by using the refractive index spectrum of the provisional specimen 111 and the time difference between the temporal waveform representing the reflected pulse B (212) and the temporal waveform representing the reflected pulse C (213) illustrated in FIG. 4B (S711). Then, the information acquiring unit 107 calculates the absorption coefficient spectrum $\alpha_{sam}$ and the extinction coefficient spectrum $\kappa_{sam}$ of the specimen 111 from Expression (8) (S712), and also calculates the refractive index spectrum $n_{sam}$ of the specimen 111 again by using the extinction coefficient spectrum $\kappa_{sam}$ (S713).

Subsequently, the information acquiring unit 107 substitutes the value of the refractive index spectrum $n_{sam}$ obtained in step S713 for the provisional refractive index spectrum used in step S711, and repeats the calculations in steps S711 to S713 until the values of the thickness of the specimen 111 and the complex refractive index spectrum (the refractive index spectrum $n_{sam}$ and the extinction coefficient spectrum $\kappa_{sam}$) of the specimen 111 converge.

When it has been confirmed that the values of the complex refractive index spectrum and the thickness of the specimen 111 have converged in step S714, the information acquiring unit 107 performs a process that corresponds to the process from steps S308 to S310 in the first embodiment thereafter. Thus, the information acquiring unit 107 acquires the information on the specimen 111.

In the above configuration, the apparatus 100 can acquire the information on the specimen 111 without using the amount of change in the phase of the terahertz wave 210 that occurs while the terahertz wave 210 travels through the plate-like member 110. Even if the thickness of the specimen 111 is unknown, the thickness of the specimen 111 and the information on the specimen 111 can be acquired by performing both the measurement of the specimen-less area 402 and convergence calculation. Hence, in an imaging process performed in the planar direction, even if the thickness of the plate-like member 110 or the thickness of the specimen 111 is not uniform, such variations in the thickness are allowable. Therefore, the optical characteristics of the specimen 111 can be acquired with high accuracy.

Fifth Embodiment

Figure 8:
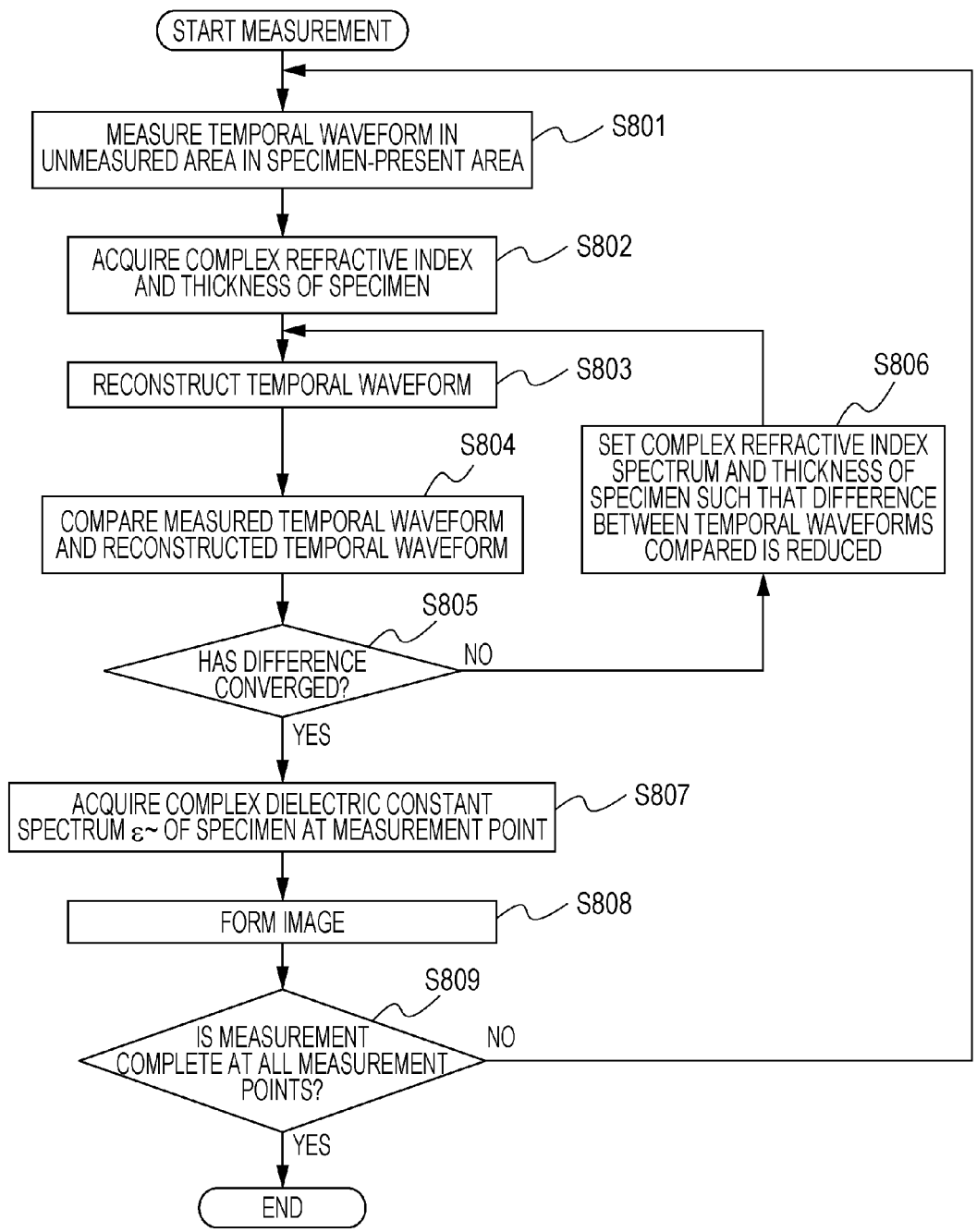
FIG. 8 is a flowchart illustrating an information acquiring method according to a fifth embodiment.

A fifth embodiment will now be described. Description of details that are common to those described above is omitted. An information acquiring apparatus according to the fifth embodiment has the same configuration as the apparatus 100 according to the first embodiment. In the fifth embodiment, a step of further improving the measurement accuracy is added to the information acquiring method according to any of the above embodiments. Specifically, the temporal waveform is reconstructed by using the information, the thickness, and so forth of the specimen 111 that are acquired by the method according to any of the above embodiments, and the reconstructed temporal waveform and the measured temporal waveform are compared. Then, the information, the thickness, and so forth of the specimen 111 are changed such that the difference between the two temporal waveforms becomes small. Thus, the accuracy of the acquired information is improved. The storage unit 119 of the apparatus 100 according to the fifth embodiment stores programs corresponding to steps of a flowchart illustrated in FIG. 8. The CPU reads the programs and executes the programs, whereby the steps are performed.

First, the waveform acquiring unit 106 acquires a temporal waveform representing the terahertz wave 210 by using the results of the detection of the reflected terahertz wave 215 that has been performed by the detecting unit 102 (S801). The information acquiring unit 107 acquires the information, the thickness $d_{sam}$, and so forth of the specimen 111 from the acquired temporal waveform by the method according to any of the first to fourth embodiments (S802). Subsequently, the information acquiring unit 107 reconstruct the temporal waveform by using the information, the thickness $d_{sam}$, and so forth of the specimen 111 acquired as described above (S803). In this step, the temporal waveform is reconstructed by using the complex refractive index spectrum (the refractive index spectrum $n_{sam}$ and the extinction coefficient spectrum $\kappa_{sam}$) and the thickness $d_{sam}$ of the specimen 111.

Subsequently, the information acquiring unit 107 compares the reconstructed temporal waveform and the measured temporal waveform, and detects the difference between the two (S804). Exemplary items to be compared may be, but are not limited to, the delay time of the reflected pulse C (213) with respect to the reflected pulse B (212), and the peak values or shapes of the respective reflected pulses A to C (211 to 213). Then, the process proceeds to step S805, in which it is checked whether or not the difference between the two temporal waveforms has converged. If the information acquiring unit 107 has determined that the difference has not converged yet, the information acquiring unit 107 sets at least one of the complex refractive index spectrum and the thickness $d_{sam}$ of the specimen 111 to a value that reduces the difference (S806). Then, the process returns to step S803, in which the temporal waveform is reconstructed and two temporal waveforms are compared (S804).

The information acquiring unit 107 performs the process of steps S803 to S806 until the difference between the reconstructed temporal waveform and the measured temporal waveform converges. If the information acquiring unit 107 has determined that the difference has converged in step S805, the process proceeds to step S807. Steps S807 to S809 correspond to steps S308 to S310 in the first embodiment.

In the apparatus 100 according to the fifth embodiment, the optical characteristics of the specimen 111 can be acquired without using the amount of change in the phase of the terahertz wave 210 that occurs while the terahertz wave 210 travels through the plate-like member 110. Furthermore, since the reconstructed temporal waveform and the measured temporal waveform are compared and convergence calculation is repeated such that the difference between the two waveforms becomes small, the information on the specimen 111 can be acquired with much higher accuracy. In addition, optical characteristics of the specimen 111 with high frequency resolution can be acquired.

Sixth Embodiment

Figure 9:
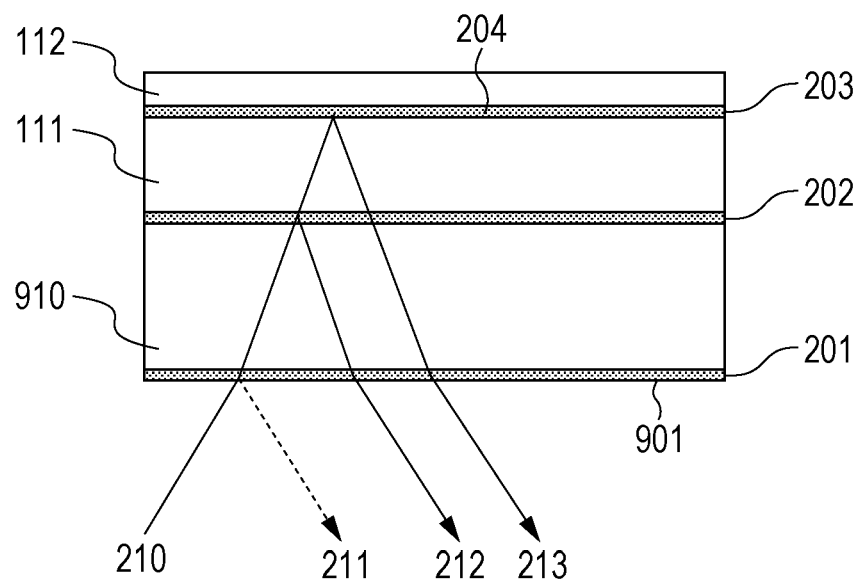
FIG. 9 illustrates a plate-like member according to a sixth embodiment.

In a sixth embodiment, a modification of the plate-like member 110 will be described with reference to FIG. 9. FIG. 9 illustrates the configuration of a plate-like member 910 according to the sixth embodiment. Description of details that are common to those described above is omitted. An information acquiring apparatus according to the sixth embodiment has the same configuration as the apparatus 100 according to the first embodiment.

The plate-like member 910 according to the sixth embodiment includes an antireflection film 901 provided on the front surface thereof, i.e., at the interface 201. Considering the refractive index of the plate-like member 110, the antireflection film 901 may be a multilayer film in which at least two layers each having an appropriate refractive index and an appropriate thickness are stacked, or a structure having microscopic surface irregularities that are of a size smaller than or equal to the wavelength of the terahertz wave 210.

By modifying the plate-like member 110 into the plate-like member 910 as described above, the reflection of the terahertz wave 210 by the front surface of the plate-like member 910 is suppressed. Therefore, the terahertz wave 210 with much higher intensity can be applied to the specimen 111. Furthermore, multiple reflection in the plate-like member 910 can be reduced. Therefore, the information on the specimen 111 can be obtained with much higher accuracy.

Seventh Embodiment

In a seventh embodiment, materials are sorted by using the apparatus 100. Specifically, sorting of plastic materials, sorting of plastic materials of the same kind on the basis of the difference in additives contained therein, and so forth are performed. The apparatus 100 according to the seventh embodiment is applicable to, for example, recycling of plastic materials, monitoring performed in a process of manufacturing plastic materials, and so forth. Description of details that are common to those described above is omitted.

An exemplary case of material sorting for recycling plastic materials will now be described. In the recycling of plastic materials, the plastic materials are sorted not only by the difference between the plastic materials themselves. Occasionally, the plastic materials need to be sorted by the difference in additives contained in the plastic materials if the plastic materials are of the same kind. If plastic materials of the same kind are recycled without being sorted by the difference in additives thereof, the original physical characteristics of the plastic materials might not be exerted even if they are of the same kind. Hence, even if such plastic materials are treated for recycling, they might not be reused depending on the usage after being recycled.

The amount of additives contained in plastic materials is very small. Therefore, information, such as optical characteristics, on plastic materials need to be acquired with high accuracy. If plastic materials are each taken as the specimen 111 and information thereon is acquired by using the apparatus 100, the information on the plastic materials can be acquired with high accuracy. By using the results thus obtained, the plastic materials can be sorted by the difference therebetween or, if they are of the same kind, by the difference in additives contained therein.

Eighth Embodiment

In an eighth embodiment, the apparatus 100 is used for distinguishing the difference in the state of bond in water contained in a biotissue, food, medicine, or the like. In the eighth embodiment, a substance containing water, such as a biotissue, food, medicine, or the like, is taken as the specimen 111. The water contained in the specimen 111 includes free water and bound water. The free water exhibits the same physical characteristics as water contained in the bulk portion of the substance. The bound water has a weak hydrogen bond to the substance. Since the state of bond is different between the free water and the bound water, the function of the free water and the function of the bound water in the substance are different in accordance with the difference in the state of bond. The content of the free water and the content of the bound water may also be different in accordance with the state of the specimen 111.

For example, in the case of a biotissue, the proportions of free water and bound water in a cancer cell and the proportions of free water and bound water in a normal cell are different. Therefore, if the difference in the state of bond in water can be distinguished, there is a possibility that any cancer cells included in the biotissue can be identified on the basis of the difference in the composition, such as the content, between the free water and the bound water. In the case of food, free water is used for multiplication of microorganisms, whereas bound water is bonded to any constituents, such as protein or hydrocarbon, of the food and is not used for multiplication of microorganisms. In the case of medicine, particularly in a case of an ointment, if the proportion of free water is high, the ointment quickly dries, leading to quality deterioration.

Some pieces of information that contribute to the identification of the state of bond in water is contained in the frequency band corresponding to terahertz wave, particularly, a frequency band of 1.2 THz or shorter. The pieces of information that contribute to the identification of the state of bond in water include, for example, the complex dielectric constant in a frequency band of 1.2 THz or shorter. Hence, if information on the specimen 111 is acquired by using the apparatus 100, the state of bond in water can be identified by using the information on the specimen 111. The apparatus 100 is capable of acquiring information on the specimen 111 with high accuracy without using the amount of change in the phase and is therefore useful in identifying the state of bond in water.

Example 1

A specific example of the first embodiment will now be described. Description of details that are common to those described above is omitted. An information acquiring apparatus according to Example 1 had the same configuration as the apparatus 100.

The plate-like member 110 was made of crystal that was cut along a z face (z-cut crystal). The z-cut crystal was sufficiently transmissive with respect to terahertz wave so that the absorption was ignorable. The thickness of the plate-like member 110 was about 1 mm, and the parallelism of the plate-like member 110 was 10 µm, which corresponds to the standard machining accuracy. The complex refractive index spectrum of the z-cut crystal in a terahertz domain had been acquired in advance by using another measuring instrument.

The specimen 111 was glycerin. The reflecting member 112 was formed by depositing a gold thin film on a silicon wafer. The gold thin film was to function as the reflecting surface 204 made of a conductive material. A frame having a thickness of 1 mm was placed on the plate-like member 110, and glycerin was dropped onto an area surrounded by the frame. Lastly, the reflecting member 112 was placed over the frame, whereby the area enclosed by the plate-like member 110, the reflecting member 112, and the frame was filled with the glycerin.

The terahertz wave 210 generated by the generating unit 101 was applied to the glycerin as the specimen 111 through the plate-like member 110 made of z-cut crystal. The point of application of the terahertz wave 210 was adjusted by causing the control unit 105 to move the scanning stage 109.

While the optical delay unit 103 was moved by 1 µm every time the point of application was changed, the terahertz wave 215 was detected by the detecting unit 102. In the detection, the detecting unit 102 detected the terahertz wave 215 at a total of 16834 points. The time elapsed for the detection was about 109 ps. The waveform acquiring unit 106 acquired a temporal waveform from the results of the detection performed by the detecting unit 102.

Figure 10:
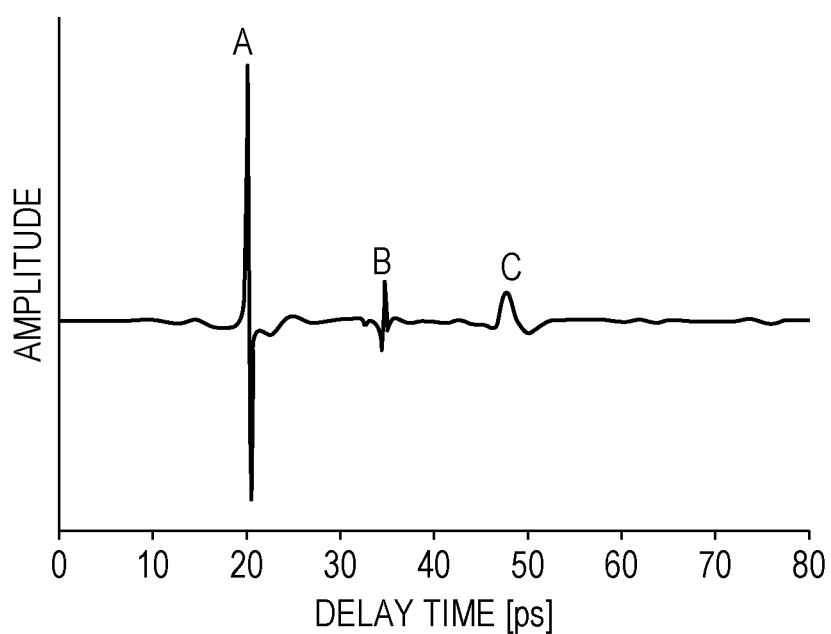
FIG. 10 is a chart illustrating a temporal waveform of the terahertz wave acquired in Example 1.

FIG. 10 illustrates the temporal waveform representing the specimen 111 that was acquired in Example 1. A reflected pulse A (211) corresponds to a portion of the radiation that was reflected by the front surface (interface) 201 of the plate-like member 110 made of z-cut crystal. A reflected pulse B (212) corresponds to a portion of the radiation that was reflected by the interface 202 between the plate-like member 110 and the specimen 111. A reflected pulse C (213) corresponds to a portion of the radiation that was reflected by the interface 203 between the specimen 111 and the reflecting surface 204.

The information acquiring unit 107 separated the reflected pulses A to C (211 to 213) from the temporal waveform. The temporal waveform was divided into portions each containing a peak representing a corresponding one of the reflected pulses A to C (211 to 213), the portions each spreading over a length corresponding to 2048 points, or a delay time of about 13.6 ps, with the peak being at the center. The divided portions of the temporal waveform were each subjected to Fourier transformation, whereby respective amplitude spectra were obtained. The amplitude spectra were each squared, whereby intensity spectra $I_A$, $I_B$, and $I_C$ corresponding to the respective reflected pulses A to C (211 to 213) were obtained.

The reflectance spectrum $R_A$ at the interface 201 had been obtained in advance from the complex refractive index spectrum of the z-cut crystal functioning as the plate-like member 110 and was about 0.127 in a frequency band of 0.1 THz or higher and 4 THz or lower. The absorption by the z-cut crystal was about 0.1 [cm$^{-1}$]. The variation in the thickness of the plate-like member 110 was about 10 μm. Therefore, the influence of the variation in the thickness of the plate-like member 110 in Expression (7) was ignorable. Hence, the reflectance spectrum $R_B$ at the interface 202 was acquired by using Expression (7). Consequently, The reflectance spectrum $R_B$ was 0.006 to 0.04 in a frequency band of 0.1 THz or higher and 3 THz or lower.

The information acquiring unit 107 calculated the absorption coefficient spectrum $\alpha_{sam}$ of glycerin in the terahertz domain by using the reflectance spectrum $R_B$ and Expression (8). The absorption coefficient spectrum $\alpha_{sam}$ generally monotonously increased toward the high-frequency side and was 10 to 200 [cm$^{-1}$] in a frequency band of 0.1 THz or higher and 2 THz or lower. Any signals representing the absorption coefficient spectrum $\alpha_{sam}$ that is on the high-frequency side with respect to 2 THz was not observable because the signal was attenuated by the absorption of glycerin.

Subsequently, the information acquiring unit 107 acquired the extinction coefficient spectrum $\kappa_{sam}$, which was an imaginary part of the complex refractive index spectrum, from the absorption coefficient spectrum $\alpha_{sam}$, and also acquired the refractive index spectrum $n_{sam}$, which was the real part of the complex refractive index spectrum of glycerin, from Expression (5). The refractive index spectrum $n_{sam}$ generally monotonously decreased to 1.7 to 2.0 in a frequency band of 0.1 THz or higher and 2 THz or lower. Then, the information acquiring unit 107 further acquired the complex dielectric constant spectrum $\in^-$ at 0.1 to 2 THz by using Expression (9).

Example 2

Another specific example of the above embodiments will now be described. Description of details that are common to those described above is omitted. An information acquiring apparatus and an information acquiring method according to Example 2 are the same as those described in the first embodiment.

The plate-like member 110 was made of z-cut crystal, as in Example 1. Four kinds of acrylonitrile-butadiene-styrene (ABS) resin plates containing respectively different additives were each taken as the specimen 111. The size of each ABS resin plate was 25 mm by 25 mm by 1 mm. In a case where the specimen 111 is solid, there is a possibility that air may be interposed between the plate-like member 110 and the specimen 111 (at the interface 202) or between the reflecting member 112 and the specimen 111 (at the interface 203) and hinder accurate measurement. To avoid such a situation, a liquid that absorbs only a little amount of terahertz wave and is difficult to evaporate may be applied to the interface 202 or 203, and the two members are pasted to each other. In Example 2, 3 μl of linoleic acid was dropped onto the interface 202 and the interface 203 so that air was excluded.

In general, if such a linoleic acid layer has a thickness of ¹⁄₂₀ or smaller than the wavelength of the terahertz wave to be applied thereto, the results of measurement are not affected. In Example 2, the thickness of the linoleic acid layer after the plate-like member 110, the specimen 111, and the reflecting member 112 were stacked was 10 μm or smaller.

Plastic materials, even if they are resin plates made from the same ingredients, exhibit different refractive index spectra in the terahertz domain in accordance with the difference in additives contained therein. The refractive indices of the four kinds of ABS resin plates employed in Example 2 in a wavelength range of 0.5 THz or higher and 3 THz or lower fell within a range of 1.62 to 1.68, and the difference in the refractive index that is attributed to the difference in the kind of the additives was about 0.002. To distinguish such a difference, the error in the measurement of refractive index needs to be ±0.001 or smaller, which in general requires high accuracy measurement.

In the information acquiring apparatus according to Example 2, information on the specimen 111 can be acquired without using the amount of change in the phase. Therefore, the measurement error attributed to the terahertz wave traveling through the plate-like member 110 can be reduced. Hence, the information acquiring apparatus according to Example 2 is useful as an apparatus for distinguishing the difference in additives contained in plastic materials of the same kind.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, the term "spectrum" such as "refractive index spectrum" or "extinction coefficient spectrum" used herein refers to optical characteristics at different frequencies. In each of the above embodiments, the spectra of different optical characteristics are acquired as information on the specimen. However, the present invention is not limited to such a case. Information on the specimen may be acquired on the basis of an arbitrary frequency.

While each of the above embodiments concerns a case where the optical delay unit 103 changes the optical path length of the ultrashort pulsed laser from the light source 104 to the generating unit 101, the optical delay unit 103 may be configured to change the optical path length from the light source 104 to the detecting unit 102.

This application claims the benefit of Japanese Patent Application No. 2013-191797, filed Sep. 17, 2013 and Japanese Patent Application No. 2014-166865, filed Aug. 19, 2014, which are hereby incorporated by reference herein in their entirety.

What is claimed is:

1. An information acquiring apparatus that acquires information on a specimen by applying a terahertz wave to the specimen through a plate-like member, the specimen being provided between a reflecting member and the plate-like member, the reflecting member having a reflecting surface that reflects the terahertz wave, the apparatus comprising:
   an applying unit configured to apply the terahertz wave to the specimen;
   a detecting unit configured to detect the terahertz wave reflected from the specimen; and
   an information acquiring unit configured to acquire the information on the specimen by using at least a first temporal waveform, which is acquired from a result of detection performed by the detecting unit, representing a portion of the terahertz wave that is reflected by an interface between the specimen and the reflecting surface of the reflecting member and a second temporal waveform, which is acquired from the result of detection performed by the detecting unit, representing a portion of the terahertz wave that is reflected by an interface between the plate-like member and the specimen,
   wherein the information acquiring unit acquires the information on the specimen by using a ratio of a first intensity spectrum obtained from the first temporal waveform to a second intensity spectrum obtained from the second temporal waveform.

2. The information acquiring apparatus according to claim 1, wherein the information acquiring unit acquires the first intensity spectrum by performing a Fourier transformation on the first temporal waveform and acquires the second intensity spectrum by performing a Fourier transformation on the second temporal waveform.

3. The information acquiring apparatus according to claim 1, wherein the reflecting surface exhibits a reflectance spectrum of 90% or higher with respect to the terahertz wave emitted from the applying unit.

4. The information acquiring apparatus according to claim 1, wherein the reflecting member includes a conductive member that exhibits a reflectance spectrum of 90% or higher with respect to the terahertz wave emitted from the applying unit.

5. The information acquiring apparatus according to claim 1, wherein the reflecting member includes a substrate and a conductive film provided on a surface of the substrate, the conductive film exhibiting a reflectance spectrum of 90% or higher with respect to the terahertz wave emitted from the applying unit, the conductive film serving as the reflecting surface.

6. The information acquiring apparatus according to claim 1, wherein the information acquiring unit acquires the information on the specimen by further using a reflectance spectrum acquired at the interface between the plate-like member and the specimen, the reflectance spectrum being acquired from a ratio of the second intensity spectrum to an intensity spectrum of a portion of the terahertz wave that is reflected by a front surface of the plate-like member, a thickness of the plate-like member, and an absorption coefficient spectrum of the plate-like member.

7. The information acquiring apparatus according to claim 6, wherein the information acquiring unit acquires the thickness of the plate-like member from a difference between a time when a temporal waveform representing a portion of the terahertz wave that is applied to a specimen-less area of the plate-like member and is reflected by the front surface of the plate-like member is detected and a time when a temporal waveform representing a portion of the terahertz wave that is applied to the specimen-less area and is reflected by a back surface of the plate-like member is detected, the specimen being absent between the plate-like member and the reflecting member in the specimen-less area.

8. The information acquiring apparatus according to claim 6, wherein the information acquiring unit acquires optical characteristics of the specimen as the information on the specimen.

9. The information acquiring apparatus according to claim 1,
   wherein the applying unit applies the terahertz wave to each of a specimen-less area of the plate-like member in which the specimen is absent between the plate-like member and the reflecting member and a specimen-present area of the plate-like member in which the specimen is present between the plate-like member and the reflecting member, and
   wherein the information acquiring unit acquires the information on the specimen by further using a reflectance spectrum acquired at the interface between the plate-like member and the specimen, the reflectance spectrum being acquired from a ratio of the second intensity spectrum to an intensity spectrum of a portion of the terahertz wave that is reflected by a front surface of the plate-like member in the specimen-present area, a ratio of an intensity spectrum of a portion of the terahertz wave that is reflected by a back surface of the plate-like member in the specimen-less area to an intensity spectrum of a portion of the terahertz wave that is reflected by a front surface of the plate-like member in the specimen-less area, and an absorption coefficient spectrum of the plate-like member.

10. The information acquiring apparatus according to claim 9, wherein the information acquiring unit acquires optical characteristics of the specimen as the information on the specimen.

11. The information acquiring apparatus according to claim 1, wherein the terahertz wave includes pulsed waves.

12. The information acquiring apparatus according to claim 1, wherein a complex refractive index of the plate-like member is known.

13. The information acquiring apparatus according to claim 1, wherein the plate-like member includes an antireflection film provided on a front surface.

14. The information acquiring apparatus according to claim 1,
   wherein the specimen is a plastic material, and
   wherein the information acquiring unit acquires the information on the specimen and, based on the acquired information on the specimen, identifies a kind of the plastic material and a kind of an additive contained in the plastic material.

15. The information acquiring apparatus according to claim 1,
   wherein the specimen is a biotissue, and
   wherein the information acquiring unit acquires the information on the specimen and, based on the acquired information on the specimen, distinguishes free water and bound water contained in the specimen from each other.

16. An information acquiring method in which information on a specimen is acquired by applying a terahertz wave to the specimen through a plate-like member, the specimen being provided between a reflecting member and the plate-like member, the reflecting member having a reflecting surface that reflects the terahertz wave, the method comprising:
  applying the terahertz wave to the specimen;
  detecting the terahertz wave reflected by the specimen; and
  acquiring the information on the specimen by using at least a first temporal waveform, which is acquired from a result of detection performed in the detecting, representing a portion of the terahertz wave that is reflected by an interface between the specimen and the reflecting surface of the reflecting member, and a second temporal waveform, which is acquired from the result of detection performed in the detecting, representing a portion of the terahertz wave that is reflected by an interface between the plate-like member and the specimen,
  wherein the acquiring acquires the information on the specimen by using a ratio of a first intensity spectrum obtained from the first temporal waveform to a second intensity spectrum from the second temporal waveform.

17. A non-transitory computer readable storage medium comprising a program causing a computer to execute the method according to claim 16.

\* \* \* \* \*